(12) United States Patent
Brown et al.

(10) Patent No.: US 7,430,765 B2
(45) Date of Patent: Oct. 7, 2008

(54) INFANT HATS, CAPS, BONNETS, AND HOODS WITH PADDED PRESSURE RELIEF REGION

(75) Inventors: Susan Matthews Brown, Golden, CO (US); Kristin A. Tidwell, Denver, CO (US); Sheila Littlehorn, Littleton, CO (US)

(73) Assignee: The Boppy Company, Golden, CO (US)

( * ) Notice: Subject to any disclaimer, the term of this patent is extended or adjusted under 35 U.S.C. 154(b) by 152 days.

(21) Appl. No.: 11/363,588

(22) Filed: Feb. 27, 2006

(65) Prior Publication Data

US 2007/0199151 A1 Aug. 30, 2007

(51) Int. Cl.
*A42B 1/00* (2006.01)
(52) U.S. Cl. ........................ 2/202; 2/204; 2/267; 2/410; 2/173.5; 2/205; 128/116.1; 128/112.1; 602/17; 5/603; 5/622; 5/655; 5/636
(58) Field of Classification Search ............... 2/204, 2/267, 410, 173.5, 202, 205; 128/116.1, 128/112.1; 602/17; 5/603, 622, 655, 636
See application file for complete search history.

(56) References Cited

U.S. PATENT DOCUMENTS

| 4,434,513 A | | 3/1984 | Welch | |
| 4,581,773 A | * | 4/1986 | Cunnane | 2/204 |
| 5,075,903 A | * | 12/1991 | Richoux | 2/411 |
| 5,261,134 A | | 11/1993 | Matthews | |
| 5,661,861 A | | 9/1997 | Matthews | |
| 6,038,720 A | | 3/2000 | Matthews et al. | |
| 6,055,687 A | | 5/2000 | Matthews | |

(Continued)

OTHER PUBLICATIONS

Heads Up, Gold Bug, 1998.

(Continued)

*Primary Examiner*—Gary L. Welch
*Assistant Examiner*—Alissa J Tompkins
(74) *Attorney, Agent, or Firm*—Townsend and Townsend and Crew LLP

(57) ABSTRACT

The invention generally relates to articles which may be used as headwear for infants that address issues related to flat head syndrome. In a first aspect, an article of headwear for an infant is provided. The headwear is configured to reduce pressure at the rear portion of the head when the infant is lying or reclining in the supine position. The headwear generally includes a head receiving portion having at least a top region and rear region for covering at least the top and rear portions of the head of the infant. In accordance with the invention, the headwear also includes support cushion positioned in the rear region of the head receiving portion. The support cushion is configured to support at least the rear portion of the head of the infant and to at least partially surround a pressure relief region. The pressure relief region is configured to receive at least a portion of the rear portion of the head such that pressure applied to the rear portion of the head is reduced when lying or reclining in the supine position. Methods for reducing pressure at the rear region of an infant's head while lying or reclining in the supine position are also provided.

15 Claims, 3 Drawing Sheets

U.S. PATENT DOCUMENTS

| | | |
|---|---|---|
| 6,119,873 A | 9/2000 | Matthews |
| 6,240,570 B1 * | 6/2001 | Wu .................................. 2/410 |
| 6,321,403 B1 | 11/2001 | Matthews |
| 6,427,253 B1 * | 8/2002 | Penny ............................ 2/412 |
| 6,842,914 B1 * | 1/2005 | Broadway ...................... 2/425 |
| 7,103,923 B2 * | 9/2006 | Picotte ........................... 2/412 |
| 2004/0015118 A1 * | 1/2004 | Sklar et al. ..................... 602/74 |

OTHER PUBLICATIONS

Nojo Double Head Support, Crown rafts Infant Products, 1999.
Graco, All-in-one Infant Support, Graco Children's Products Inc., 2000.
Infant Head Rest, Kidsline.

\* cited by examiner

INFANT HATS, CAPS, BONNETS, AND HOODS WITH PADDED PRESSURE RELIEF REGION

BACKGROUND OF THE INVENTION

Medical advice now suggests that infants should be placed on their backs or side when sleeping in order to reduce the number of incidents of Sudden Infant Death Syndrome (SIDS). A variety of sleep positioners have been developed to help maintain infants in the supine position. However, using these sleep positioners can sometimes lead to a situation where the back of the baby's head becomes flattened, commonly known as "flat head" syndrome, which may cause concern to some parents.

There are several infant support pads to address issues related to flat head syndrome. They include different types of foam construction, foam pad contouring, shapes, angles and contour pillows. However, there is still a need for improved pressure relief designs to better accommodate an infant's movements.

SUMMARY OF THE INVENTION

The invention generally relates to articles which may be used as headwear for infants that address issues related to flat head syndrome.

In a first aspect, an article of headwear for an infant is provided. The headwear is configured to reduce pressure at the rear portion of the head when the infant is lying or reclining in the supine position. The headwear generally comprises a head receiving portion having at least a top region and rear region for covering at least the top and rear portions of the head of the infant. In accordance with the invention, the headwear also includes support cushion positioned in the rear region of the head receiving portion. The support cushion is configured to support at least the rear portion of the head of the infant and to at least partially surround a pressure relief region. The pressure relief region is configured to receive at least a portion of the rear portion of the head such that pressure applied to the rear portion of the head is reduced when lying or reclining in the supine position.

The support cushion may be comprised of fiberfill, foam, an inflatable insert, memory foam, polystyrene beads, rice, buckwheat, a gel insert, etc. In alternate embodiments, the support cushion may be comprised of a shape retaining material to retain the shape of the head of infant.

In some embodiments, the pressure relief region may comprise a recessed portion in the support cushion, which may optionally comprise an aperture extending through the support cushion. The recessed portion may have a variety of shapes. By way of example, the recessed portion may have a cross-sectional shape consisting of a circle, an oval, an ellipse, or combinations of these shapes. The support cushion may have an outer periphery consisting of a circular geometry, a semicircular geometry, or a rectangular geometry.

In another aspect, a method for reducing pressure at the rear region of an infant's head while lying or reclining in the supine position is provided. The methods of the invention generally comprise providing an article of headwear, wherein the headwear comprises a head receiving portion and a support cushion. Again, the support cushion is configured to support at least the rear portion of the head of the infant and to at least partially surround a pressure relief region, and the pressure relief region is configured to receive at least a portion of the rear portion of the head such that pressure applied to the rear portion of the head is reduced when lying or reclining in the supine position. The method further comprises placing the headwear about the infant's head, such that the headwear covers at least the top portion and rear portion of the infant's head, and placing an infant in a supine position with the infant's head resting on the cushion support region, and with at least the rear portion of the infant's head being disposed over the pressure relief region such that pressure applied to the rear portion of the head is reduced.

DESCRIPTION OF THE SPECIFIC EMBODIMENTS

In the following description, for the purposes of explanation, numerous specific details are set forth in order to provide a thorough understanding of the present invention. It will be apparent, however, to one skilled in the art that the present invention may be practiced without some of these specific details. Although concrete embodiments will be described with reference to an article of headwear for an infant used to reduce pressure at the rear portion of the head of the infant when lying or reclining in the supine position, with minimal or no variations, the headwear may also be used to reduce pressure on an infant's head in a side-lying or reclining position. Additionally, with some minor variations, the headwear may also be sized for use by an older child or an adult, if desired.

Figure 1:
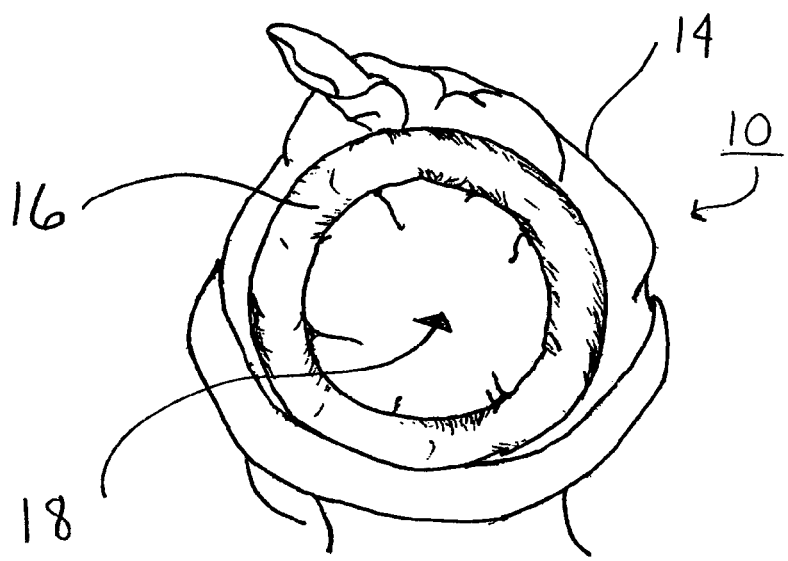
FIG. 1 illustrates a back perspective view of an exemplary embodiment of the invention.
Figure 2:
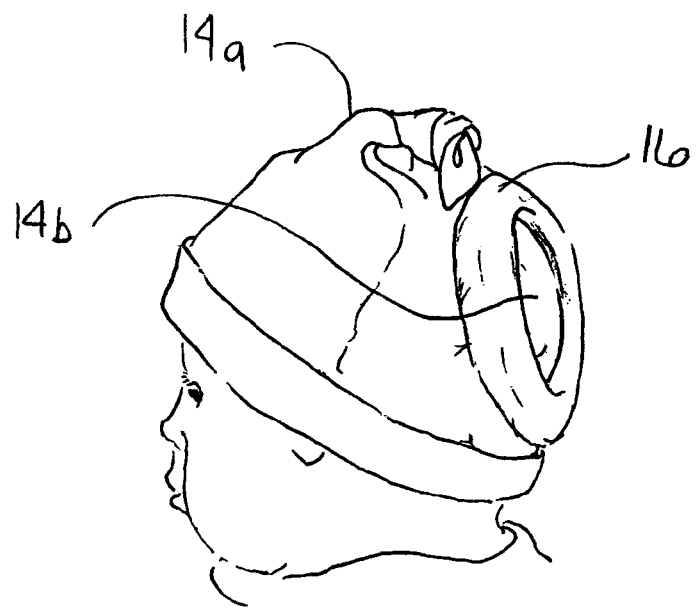
FIG. 2 illustrates a side perspective view of an exemplary embodiment of the invention.

FIG. 1 illustrates an exemplary embodiment of an article of headwear for an infant. The article of headwear may be configured in any manner known in the art, such as, but not limited to a hat, cap, bonnet, or hood. The headwear 10 includes a head receiving portion 14. The head receiving portion 14 is generally sized and shaped so as to accommodate the size and shape of a infant's head, e.g., a newborn aged infant up to an infant of about 1 year old, 2 years old, etc. With reference to FIG. 2, the head receiving portion 14 will generally include at least a top region 14a and a rear region 14b for covering at the top and rear portion of the head of an infant, respectively, when in use.

A variety of materials may be used to form head receiving portion 14. For example, in one embodiment, the head receiving portion 14 may be a quilted material formed by placing a fill material between fabric pieces. Seams may be sewn into the fabric to prevent shifting of the fill material. Alternatively, the head receiving portion 14 may be formed from any suitable fabric, stretchable fabric, or material, e.g., cotton, polyester, or blends thereof. In some embodiments, the head receiving portion 14 may have other properties to enhance the comfort of an infant. For example, the head receiving portion 14 may include a temperature regulating material. Alternately, or additionally, the head receiving portion 14 may include a scented material, such as lavender, which may have a calming effect on the infant.

The headwear 10 further includes support cushion 16. As shown in the exemplary embodiment of FIGS. 1 and 2, support cushion 16 is positioned so as to support at least the rear portion of the head of the infant, and it extends from at least a portion of the rear region 14b of the head receiving portion 14 of the headwear. The support cushion may be generally sized and shaped so as to interface with the rear portion of an infant's head. For instance, infant head circumferences may range from about 10 inches to about 20 inches. As such, the support cushion 16 may be sized and shaped so as to conform to the size of the rear portion of an infant. In certain embodiments, the support cushion may be about 3.0 inches to about 5.0 inches, from about 3.5 inches to about 4.5 inches, etc., in width. The support cushion 16 may have an outer perimeter that is generally semicircular, generally circular, generally rectangular, or another appropriate shape. As such, in certain embodiments, the support cushion 16 may be about 3.0 inches to about 5.0 inches, from about 3.5 inches to about 4.5 inches, etc. in diameter.

Figure 3A:
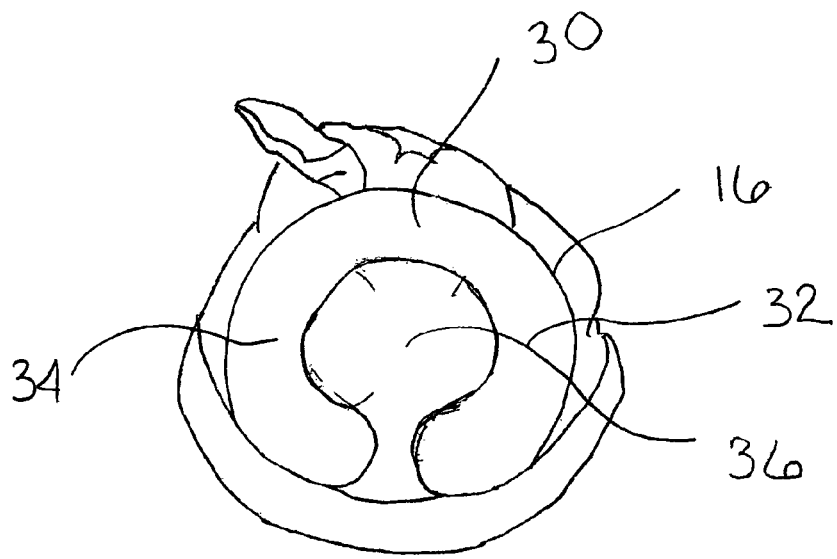
FIGS. 3A and B illustrates a back perspective view of an alternative embodiment of the invention.

In one embodiment, the support cushion may have a semicircular geometry that includes a medial region and two opposing arms with ends extending from the medial region to define an inner well region. In such embodiments, the inner well region may be shaped in any suitable manner, e.g., circular, oval, elliptical, etc. An exemplary support cushion 16 having a medial region 30 and two opposing arms 32,34 with ends defining an inner well region 36, is illustrated in FIG. 3A.

The support cushion 16 is designed to receive the back of the infant's head and at least partially surrounds or forms pressure relief region 18. By way of example, support cushion 16 may include a central aperture that extends through support cushion 16, or may be configured with a centrally recessed core. This aperture or recessed core may then define pressure relief region 18. In use, the back of the infant's head rests upon the support cushion 16 and is disposed over the pressure relief region 18. Thus, a substantial amount of pressure that would otherwise be applied to a generally small region on the back of the infant's head when lying in a supine position to be distributed to other locations on the head. This may eliminate or reduce the flattening of the back of the infant's head that may occur over time from lying in a supine position.

Figure 3B:
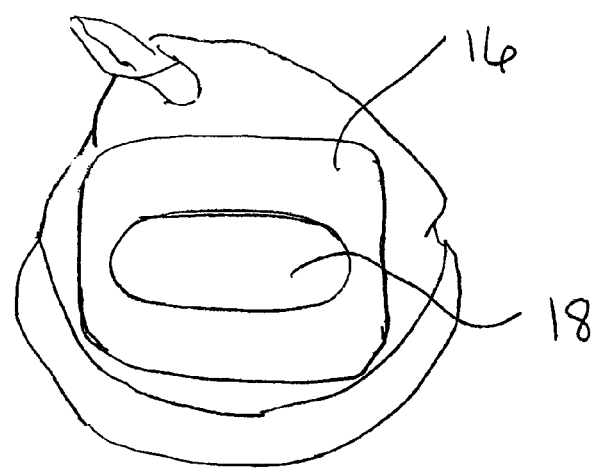

The pressure relief region 18 may be configured in a number of ways, such as, for example, an aperture, recessed portion, or depression surrounded at least in part by the support cushion 16, a material that is less resilient that the support cushion 16, or the like. The outer perimeter of the pressure relief region 18 may be varied By way of example, the outer perimeter may be circular, square, rectangular, oval, elliptical, arcuate, or the like. Further, any combination of outer perimeter shape of the pressure relief region and support cushion geometry may be used. For instance, circular support cushion geometry may be used with circular, square, rectangular, oval, elliptical, arcuate, etc. pressure relief region outer perimeter shape. By way of non-limiting example, FIG. 3B illustrates a rectangular support cushion 16 geometry in combination with an elliptical pressure relief region 18 outer perimeter shape.

In certain embodiments, the pressure relief region may be sized and shaped so as to have a width or diameter of, e.g., about 1.5 inches to about 3 inches, about 2 inches to about 2.5 inches, etc. In certain embodiments, the pressure relief region may be formed from the inner well region 36 of the support cushion 16. As previously described, in use, the back of the infant's head rests on support cushion 16 and is positioned over the pressure relief region 18. If configured as an aperture, the back of the head may experience no pressure at this region (with the entire weight of the head being supported by the surrounding support cushion 16). Alternatively, the support cushion 16 may be configured to have a certain height, outer perimeter and/or resilience so that some of the head's weight is supported by a surface positioned below the support cushion 16.

Support cushion 16 may be secured to the exterior surface of head receiving portion 14, or may integrated within head receiving portion 14. Support cushion 16 may be secured to the head receiving portion 14 in any suitable manner known in the art, including but not limited to stitching, adhesives, hook and loop fasteners, snaps, buttons, etc. If desired, support cushion 16 may be releasably secured to head receiving portion 14. In such embodiments, support cushions of varying sizing may be provided, and releasably secured to the head receiving portion so as to customize fit and accommodate for varying head sizes and growth of the infant's head.

Support cushion 16 and pressure relief region 18 may be formed in any suitable manner known in art. For instance, support cushion 16 and/or pressure relief region 18 may be comprised of fiberfill, foam, an inflatable bladder, memory foam, polystyrene beads, rice, buckwheat, a gel insert, and combinations thereof. In certain embodiments, support cushion 16 and/or pressure relief region 18 may be formed by placing a fill material between fabric pieces. In other embodiments, support cushion 16 and/or pressure relief region 18 may be comprised of a single piece of formed material, shaped in the desired manner. By way of example, materials suitable for used in connection with the support cushion include inflatable bladders that may be filled with air or fluids, gel inserts, and viscoelastic material (e.g., memory foam or other type of material that at least partially retains the shape of the infant's head). Other exemplary materials include rubbers (including foamed rubber), padding, fibers, fiberballs, polyester fill material, fabrics, small pellets, and/or natural materials (e.g., feathers, seeds, hair). Fill materials may be used alone or in various combinations and materials other than those mentioned may also be used.

In use, the headwear 10 may be placed on the infant, with the top of infant's head being placed within the head receiving portion 14. The back of the infant's head will generally fit within the aperture defined by pressure relief region 18. The sides of the head rest upon the cushion support region. Depending on the resilience of support cushion 16, its height, and the shape and size of the aperture, the back of the head may rest upon a surface below support cushion 16, or may be suspended above the surface. In this way, the pressure applied to the back of the head is greatly reduced or eliminated to prevent flattening of the back of the head, as well as providing additional comfort to the infant.

Figure 4:
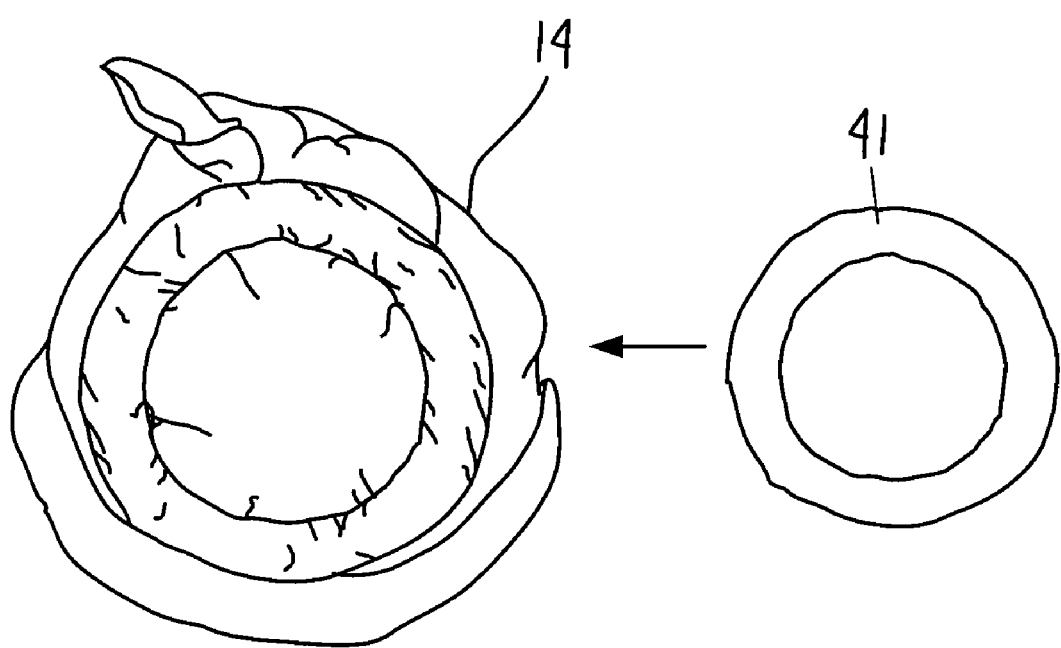
FIG. 4 illustrates a back perspective view of an alternative embodiment of the invention.

In other aspects of the invention, kits comprising a head receiving portion and cushioning supports of varying sizes and shapes are provided. The cushioning supports may be configured so as to be releasably secured to the head receiving portion, and may be provided in a variety of sizes and shapes so as to accommodate a variety infant head sizes and so as to provide a custom fit of the headwear appropriate for the particular user. FIG. 4 illustrates an exemplary kit comprising head receiving portion 14 with a cushioning support in place, and also comprising additional cushioning support 41 of a different size. Again, any suitable manner for securing the cushioning supports may be used, including but not limited to hook and loop fasteners. Further, the cushion supports may be secured to the exterior surface of the head receiving portion, or may be integrated within the head receiving portion. For instance, the cushioning support may be secured within an interior pocket to provide for a more streamlined look to the headwear and to provide a more secure fastening of the support cushion. The invention also contemplates methods for customizing pressure reducing headwear.

The invention has now been described in detail for the purposes of clarity of understanding. However, it will be appreciated that certain changes and modifications may be practiced within the scope of the appended claims.

What is claimed is:

1. An article of headwear for an infant to reduce pressure at the rear portion of the head when lying or reclining in the supine position, the headwear comprising:
   a head receiving portion having at least a top region and rear region configured to cover at least the top and rear portions of the head of the infant; and
   a support cushion positioned in the rear region of the head receiving portion;
   wherein the support cushion has an outer cushion support region configured to support the head of the infant by contact at the sides of the rear portion of the head and is configured to at least partially surround a pressure relief region, and wherein the entire portion of the pressure relief region at least partially surrounded by the cushion support region is recessed so as to provide a hollow cavity relative to the outer cushion support region and is configured to receive at least a portion of the rear portion of the head such that pressure applied to the rear portion of the head is reduced when lying or reclining in the supine position.

2. The headwear of claim 1, wherein the support cushion comprises a shape retaining material that retains at least a portion of a shape of the infant's head.

3. The headwear of claim 1, wherein the support cushion comprises a cushion formed from a material selected from the group consisting of: fiberfill, foam, an inflatable bladder, memory foam, polystyrene beads, rice, buckwheat, a gel insert, and combinations thereof.

4. The headwear of claim 1, wherein the recessed portion comprises an aperture extending through the support cushion.

5. The headwear of claim 1, wherein the recessed portion has a cross-sectional shape that is selected from a group consisting of a circle, an oval, an ellipse and combinations thereof.

6. The headwear of claim 1, wherein the support cushion has an outer periphery consisting of one of a circular geometry, a semicircular geometry, and a rectangular geometry.

7. The headwear of claim 6, wherein the outer periphery of the support cushion comprises a semicircular geometry having a medial region and two opposing arms with ends extending from the medial region to define an inner well region.

8. The headwear of claim 1, wherein the support cushion is about 3.5inches to about 4.5 inches in width, such that the support cushion is sized to interface with the rear portion of the infant's head when in use.

9. The headwear of claim 1, wherein the headwear is configured as a hat, cap, bonnet or hood.

10. A method for reducing pressure at the rear region of an infant's head while lying or reclining in the supine position, the method comprising:
    providing an article of headwear, wherein the headwear comprises a head receiving portion and a support cushion, wherein the support cushion comprises an outer cushion support region configured to support at least the rear portion of the head of the infant by contact at the sides of the rear portion of the head, and configured to at least partially surround a pressure relief region, and wherein the entire pressure relief region at least partially surrounded by the cushion support region is recessed so as to provide a hollow cavity relative to the outer cushion support region and is configured to receive at least a portion of the rear portion of the head such that pressure applied to the rear portion of the head is reduced when lying or reclining in the supine position;
    placing the headwear about the infant's head, such that the headwear covers at least the top portion and rear portion of the infant's head;
    placing an infant in a supine position with the infant's head resting on the cushion support region, and with at least the rear portion of the infant's head being disposed over the pressure relief region such that pressure applied to the rear portion of the head is reduced.

11. The headwear of claim 1, wherein the headwear is configured as a cap or bonnet.

12. The headwear of claim 1, wherein the support cushion is secured to an exterior surface of the head receiving portion.

13. The headwear of claim 1, wherein the support cushion is integrated within the head receiving portion.

14. The headwear of claim 1, wherein the support cushion is releasably secured to the head receiving portion.

15. The headwear of claim 14, further comprising multiple cushion support members that are configured to be releasably secured to the head receiving portion and that are provided in a variety of sizes, and wherein the support cushions may be interchanged to accommodate varying infant head sizes.

* * * * *